(12) United States Patent
Schreiber

(10) Patent No.: US 11,599,977 B2
(45) Date of Patent: Mar. 7, 2023

(54) IMAGE-PROCESSING OF IMAGE DATASETS OF PATIENTS

(71) Applicant: Siemens Healthcare GmbH, Erlangen (DE)

(72) Inventor: Bernd Schreiber, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 96 days.

(21) Appl. No.: 16/715,033

(22) Filed: Dec. 16, 2019

(65) Prior Publication Data

US 2020/0202501 A1    Jun. 25, 2020

(30) Foreign Application Priority Data

Dec. 20, 2018    (DE) .......................... 102018222595.8

(51) Int. Cl.
*G06T 5/20*    (2006.01)
*G06T 5/00*    (2006.01)
(Continued)

(52) U.S. Cl.
CPC .............. *G06T 5/20* (2013.01); *A61B 6/032* (2013.01); *A61B 6/5258* (2013.01); *A61B 6/54* (2013.01);
(Continued)

(58) Field of Classification Search
CPC ......... G06T 5/20; G06T 5/007; G06T 7/0014; G06T 2207/30101; G06T 2207/10116;
(Continued)

(56) References Cited

U.S. PATENT DOCUMENTS 8,942,789 B2 *  1/2015  Ostermeier ............ A61B 6/488
                                                    600/467
2011/0052030 A1 *  3/2011  Bruder ................ A61B 6/4014
                                                    382/131
(Continued)

OTHER PUBLICATIONS

Frequency split metal artifact reduction (FSMAR) in computed tomography. Medical physics, 39(4), 1904-1916 Esther Meyer, Rainer Raupach, Michael Lell, Bernhard Schmidt, Marc Kachelrieß (Year: 2012).*
"Frequency split metal artifact reduction (FSMAR) in computed tomography" Esther Meyer,Rainer Raupach,Michael Lell,Bernhard Schmidt,Marc Kachelrieß (Year: 2012).*
(Continued)

*Primary Examiner* — Vu Le
*Assistant Examiner* — Winta Gebreslassie
(74) *Attorney, Agent, or Firm* — Lempia Summerfield Katz LLC

(57) ABSTRACT

A method is provided for image-processing an image dataset acquired from a patient by a medical imaging apparatus, (e.g., an X-ray apparatus), wherein the image dataset includes image values associated with image points, and depicts an acquisition region of the patient containing at least one object, (e.g., a medical device), to be enhanced, which is represented by image values within an image-value interval. The method includes determining a non-linearly high-pass filtered enhancement dataset, which is confined to an image portion containing image values lying in the image-value interval. The method also includes determining a result dataset by adding to the image dataset the enhancement dataset weighted by a weighting value. The method further includes outputting the result dataset.

18 Claims, 3 Drawing Sheets

(51) Int. Cl.
*G06T 7/00* (2017.01)
*A61B 6/00* (2006.01)
*A61B 6/03* (2006.01)

(52) U.S. Cl.
CPC ............ *G06T 5/007* (2013.01); *G06T 7/0014* (2013.01); *G06T 2207/10116* (2013.01); *G06T 2207/30008* (2013.01); *G06T 2207/30021* (2013.01); *G06T 2207/30052* (2013.01); *G06T 2207/30101* (2013.01)

(58) Field of Classification Search
CPC ........... G06T 2207/30008; G06T 2207/30021; G06T 2207/30052; G06T 5/002; G06T 7/0012; G06T 2207/10081; G06T 2207/20192; G06T 5/008; G06T 2207/20024; G06T 5/00; G06T 2207/20028; A61B 6/5258; A61B 6/032; A61B 6/54
See application file for complete search history.

(56) References Cited

U.S. PATENT DOCUMENTS

| | | | | |
|---|---|---|---|---|
| 2011/0286651 | A1* | 11/2011 | Yu | G06T 11/005 382/131 |
| 2013/0202177 | A1* | 8/2013 | Bar-Aviv | G06T 5/002 382/128 |
| 2013/0223719 | A1 | 8/2013 | Ohishi et al. | |
| 2015/0098550 | A1* | 4/2015 | Yi | A61B 6/4233 378/62 |
| 2016/0029992 | A1* | 2/2016 | Iijima | A61B 6/547 378/62 |
| 2017/0116712 | A1* | 4/2017 | Liao | G06T 5/003 |
| 2018/0122088 | A1* | 5/2018 | Ertel | G06T 5/008 |

OTHER PUBLICATIONS

Suetens, P.: "Fundamentals of medical imaging"; Third edition. Cambridge: Cambridge University Press, 2017; pp. 8-14, 30, 45-46, 58.

* cited by examiner

9 Medical imaging apparatus
10 C-arm
11 X-ray source
12 X-ray detector
13 Operating table
14 Control apparatus
15 Display device
16 Operating device 14 Control apparatus
17 Acquisition unit
18 Filter unit
19 Low-pass filtering sub-unit
20 Subtraction sub-unit
21 Determination unit
22 Output unit

IMAGE-PROCESSING OF IMAGE DATASETS OF PATIENTS

The present patent document claims the benefit of German Patent Application No. 10 2018 222 595.8, filed Dec. 20, 2018, which is hereby incorporated by reference.

TECHNICAL FIELD

The disclosure relates to a method for image-processing an image dataset acquired from a patient by a medical imaging apparatus, (e.g., an X-ray apparatus), wherein the image dataset includes image values associated with image points, and depicts an acquisition region of the patient containing at least one object, (e.g., a medical device), to be enhanced, which is represented by image values within an image-value interval. The disclosure also relates to a medical imaging apparatus, (e.g., an X-ray apparatus), to a computer program, and to an electronically readable data storage medium.

BACKGROUND

Medical imaging, for instance X-ray imaging, although increasingly other modalities as well, (e.g., magnetic resonance imaging), is also used to facilitate assessment of the progress and/or success of surgical interventions, in particular minimally invasive interventions, on a patient. In such pre-operative, intra-operative, inter-operative, and/or post-operative imaging, it is necessary, for example, to assess to what extent a medical device, in particular an implant and/or an instrument, is correctly positioned in order to achieve the desired medical effect and/or to obtain the desired diagnostic information.

An example of such a surgical intervention, specifically a minimally invasive intervention, is placing a stent in a blood vessel of a patient. During or after placement of the stent, the practitioner performing the placement provides that the position of the stent is correct. This is made more difficult in particular if the stent is located close to other medical devices, for instance metal coils, and/or is surrounded by strongly attenuating anatomical structures, (e.g., bones). Thus, medical image datasets of an acquisition region of a patient, in which certain objects, (e.g., medical devices), are meant to be assessed, may be difficult to interpret when other anatomical structures and/or medical aids are located in the vicinity.

SUMMARY AND DESCRIPTION

The object of the disclosure is to define a facility for image processing that allows improved visualization of high-contrast objects, in particular medical devices, in a medical image dataset.

This object is achieved by a method, a medical imaging apparatus, a computer program, and an electronically readable data storage medium. The scope of the present disclosure is defined solely by the appended claims and is not affected to any degree by the statements within this summary. The present embodiments may obviate one or more of the drawbacks or limitations in the related art.

A method of the type mentioned in the introduction includes the following acts: determining a non-linearly high-pass filtered enhancement dataset, which is confined to an image portion containing image values lying in the image-value interval; determining a result dataset by adding to the image dataset the enhancement dataset weighted by a weighting value; and outputting the result dataset.

It is proposed to apply non-linear filtering, which generates an enhancement dataset which, when added to the original medical image dataset, produces a result dataset, in which the object under assessment, in particular a medical device, so for instance an implant and/or an instrument, is far more clearly discernible, without the noise level and/or surrounding objects being equally amplified and/or artifacts arising. This is achieved by applying the filtering only to regions of the medical image dataset in which the image values lie in a predetermined image-value interval, which is assigned to the object to be enhanced and thus specifies the range, (e.g., the gray-level range and/or HU-value range in X-ray imaging), in which lie image values of image points, (e.g., pixels or voxels), depicting the object to be enhanced. For high-contrast objects such as medical devices, it is possible to define in particular image-value intervals that exclude anatomical structures in the acquisition region and/or do not include as well image values of other medical aids that may be situated in the acquisition region. Thus, the non-linear filtering is applied selectively to image regions that form, or include as accurately as possible, the image portion depicting the object to be enhanced.

The image-value interval may be defined both on the basis of theoretical considerations, in particular incorporating the material properties of the object that are relevant to the imaging, and/or on the basis of prior measurements on the object, in which in particular specific calibration measurements may also be performed.

The enhancement dataset may include just the image portion that has also been filtered non-linearly, although in exemplary embodiments, it is also conceivable to include other regions at least initially, which therefore do not drop out until later.

One specific option in this case for determining the enhancement dataset provides that the following acts are carried out: determining an interim dataset by applying a non-linear low-pass filter to image points satisfying a selection condition that evaluates image values, wherein the selection condition selects an image point when an image value of the image point lies within the image-value interval; and determining the enhancement dataset by subtracting the interim dataset from the image dataset pixel by pixel.

One finding relating to the present disclosure is that low-pass filters requiring the required properties (details of which will be given later) have already been specifically proposed in the prior art and therefore may also be applied. A particular advantage in the described determination of the enhancement dataset, however, is that by subtraction, image regions of the medical image dataset that are unfiltered, (e.g., do not depict the object to be enhanced), simply drop out, and therefore a direct enhancement may be achieved by subsequent addition of the enhancement dataset to the image dataset. It is therefore provided to apply a non-linear low-pass filter to the medical image dataset, which moreover may be two-dimensional or three-dimensional. It is also the case for the non-linear low-pass filter that this filter is applied only to image points whose image values lie in the predefined image-value interval, the image-value interval containing image values of the high-contrast object to be enhanced. In the case of a medical device as the object to be enhanced, this means that in particular anatomic structures such as soft tissue, bone, or air are not filtered, which also applies to other medical aids and the like that produce image values lying outside the image-value interval. These unfiltered image points are initially retained in the interim dataset of course, but after filtering, the non-linearly high-pass filtered enhancement dataset is obtained by suitable subtraction of the low-pass filtered interim dataset from the original medical image dataset.

In the present disclosure, non-linear filtering is carried out. In this context, one embodiment provides that for the low-pass filtering, image points lying within a filter mask being used around an image point under consideration are rated according to the difference between their image value and the image value of the image point under consideration, wherein in particular more widely divergent image values result in a lower weighting, and the filtering process is performed on the basis of the rating. In one example, a bilateral filter and/or a weighted median filter may be used as the low-pass filter, because both of the low-pass filter types already provide the relevant weighting according to image-value differences.

Thus specifically an intensity weighting is performed by the non-linearity in the filter application, which weighting penalizes image-value discrepancies between neighbors that are too large, for example, image-value differences that lie significantly above the standard deviation given mainly by the noise, resulting in the associated image values being ignored, or in a far lower weighting, in the low-pass filtering. Hence, voxels that contain the object to be enhanced are not corrupted, for instance, by other objects, for example, other medical aids, in the immediate vicinity, that are also captured by the filter mask being used. It is found that it is thereby possible to achieve a particularly clear enhancement that is confined to the object to be enhanced, while at the same time amplification of noise effects may largely be avoided, and other, in particular adjacent objects, for example, anatomical structures and/or medical aids, are neither amplified nor have a detrimental effect on the image appearance, for instance as a result of artifacts from the filtering.

A further embodiment regarding the filtering process may also provide that, in particular as an additional selection condition, individual divergent image points that are located inside an area in which the image values lie within the image-value interval, which image points have an image value outside the image-value interval, are detected and also are subject to the filtering. It is hence possible to monitor whether outriders arise inside areas, or image regions, in which the image values otherwise lie within the image-value interval, (e.g., the area would be meant to be assigned to the object to be enhanced), which outriders may nonetheless still be included in the filtering, which in particular may help also to smooth the image appearance.

In one example, the object may be a medical device, e.g., a stent. Although stents are in principle high-contrast objects, the stents nonetheless may be imaged more faintly, (e.g., when the wall thickness is rather thin), than other medical aids, (e.g., coils introduced into an aneurysm). Therefore, the procedure may be used particularly advantageously for assessing a stent, because stents are significantly more discernible in the result dataset. At the same time, the noise level in the soft-tissue regions is not increased, and bone structures are not enhanced, just as is the case for other medical aids, (e.g., coils introduced into an aneurysm), which may result in a far higher intensity, (e.g., far higher image values). Thus, the image interval may be advantageously selected such that anatomical structures in the acquisition region that do not correspond to the object, and/or medical aids that do not correspond to the object, (e.g., coils in an aneurysm), are not selected for filtering. Various types of catheter are an alternative example to stents as the medical device.

The weighting value constitutes a coefficient that is meant to be selected to be greater than zero, which defines the magnitude of the enhancement and expediently is meant to be selected such that a distinct enhancement of the object to be enhanced occurs in the result dataset, without changing too much the image appearance, so that the image may continue to be interpreted in its entirety. For example, the weighting value may be selected in a range of 1 to 20, in particular 5 to 10, and/or adjusted by the user, for instance by a control.

The image dataset may be three-dimensional and exist in the form of sectional images or slice images. It is then possible to determine successively for all the sectional images or slice images an associated result image of the result dataset. In particular, it may then be conceivable to confine the image processing to portions of a total dataset, if required, for instance if enhancement is meant to be performed only in certain sectional images or slice images.

While is it conceivable and also expedient for the purpose of outputting the result dataset to store for further use and/or to transfer to another computing apparatus said result dataset, it may be provided that the result dataset is displayed, e.g., in a volume-rendered manner, as a thin-slab, maximum intensity projection, as a multiplane reconstruction, or a combination thereof. The enhancement effect produced by performing the acts of the method shows a significant improvement in the visibility of the object to be enhanced for volume rendering views (VRT), for maximum intensity projections (MIPs), thin-slab maximum intensity projections (MMIPs), and multiplane reconstructions (MRPs).

The present disclosure relates not only to the method but also to a medical imaging apparatus which includes a control apparatus configured to perform the method. All the statements relating to the method may also be applied analogously to the medical imaging apparatus, and therefore the advantages already described may also be achieved by the apparatus. In particular, the medical imaging apparatus may be an X-ray apparatus, for example, an X-ray apparatus having a C-arm, on which an X-ray source and an X-ray detector are arranged opposite one another. A C-arm X-ray apparatus of this type may be used particularly advantageously in surgical interventions on the patient, in particular minimally invasive interventions, in order to monitor the progress of the intervention and/or establish the success of the intervention. It is conceivable in particular for C-arm X-ray apparatuses to acquire projection images from different projection directions, (e.g., during rotation of the C-arm), in order to obtain thereby a basis from which a three-dimensional image dataset of the acquisition region may be reconstructed. It has already been proposed to employ other X-ray apparatuses, (e.g., computed tomography apparatuses), for use in medical interventions. Further, acquiring intra-operative or post-operative medical image datasets has also already been proposed with regard to magnetic resonance apparatuses.

The control apparatus may include at least one processor and at least one storage device. In particular, the control apparatus may implement a plurality of functional units for performing the acts of the method disclosed herein. Using a control apparatus of a medical imaging apparatus employed in particular in a surgical intervention has the advantage that the enhancement may be implemented directly, and the result dataset may be displayed, for example, on at least one display device of the medical imaging apparatus, in particular on a visual monitor, in which case the display device is advantageously situated in a position that may be seen from the operating position of the practitioner. It is also conceivable to perform the method on another computing apparatus, (e.g., a workstation or a computing apparatus of a viewing station).

A control apparatus or computing apparatus configured to perform the method may include a filter unit for determining the enhancement dataset, a determination unit for determining the result dataset, and an output unit for outputting the result dataset, in particular an output interface. The filter unit may include as sub-units a low-pass filter sub-unit and a subtraction unit. The filter unit and the determination unit may be image processors.

The medical imaging apparatus may also have an input device, via which may be selected, for example, a class of the object to be enhanced, to which class are then assigned suitable selection and/or filter parameters. Selection and/or filter parameters include, for example, parameters specifying the image-value interval, parameters specifying a filter mask, parameters specifying permitted divergences from adjacent image points, e.g., permitted image-value differences, and/or a weighting value. If applicable, it may also be possible to select the latter separately, (e.g., while the result dataset is being displayed), so that a user may select a display form to suit.

A computer program may be loaded, for example, directly into a storage device of a computing apparatus, in particular a control apparatus of a medical imaging apparatus and include program code to perform the acts of a method when the computer program is executed in the computing apparatus. The computer program may be stored on an electronically readable data storage medium, which therefore includes electronically readable control information stored thereon that includes the computer program and is configured such that it performs a method when the data storage medium is used in a computing apparatus. The data storage medium may be a non-transient data storage medium, e.g., a CD-ROM.

BRIEF DESCRIPTION OF THE DRAWINGS

Further advantages and details of the present disclosure are presented in the exemplary embodiments described below, and arise with reference to the drawings, in which.

DETAILED DESCRIPTION

Figure 1:
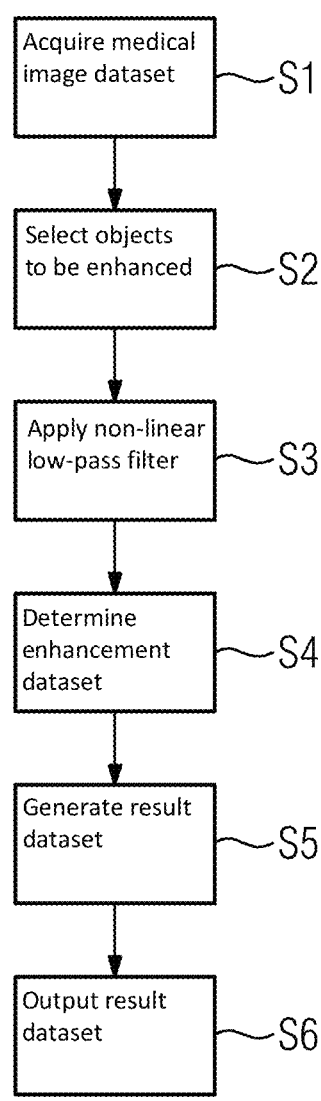
FIG. 1 depicts a flow diagram of an exemplary embodiment of the method.

FIG. 1 depicts a flow diagram of an exemplary embodiment of the method. An intention in the present case is to assess the progress or success of placing a stent in a blood vessel of a patient, for which purpose, in act S1, a corresponding medical image dataset is acquired intra-operatively or post-operatively using a medical imaging apparatus, in this case a C-arm X-ray apparatus. In this process, projection images are acquired from different projection directions, and the three-dimensional medical image dataset, which may exist in the form of sectional images or slice images, is reconstructed.

Figure 2:
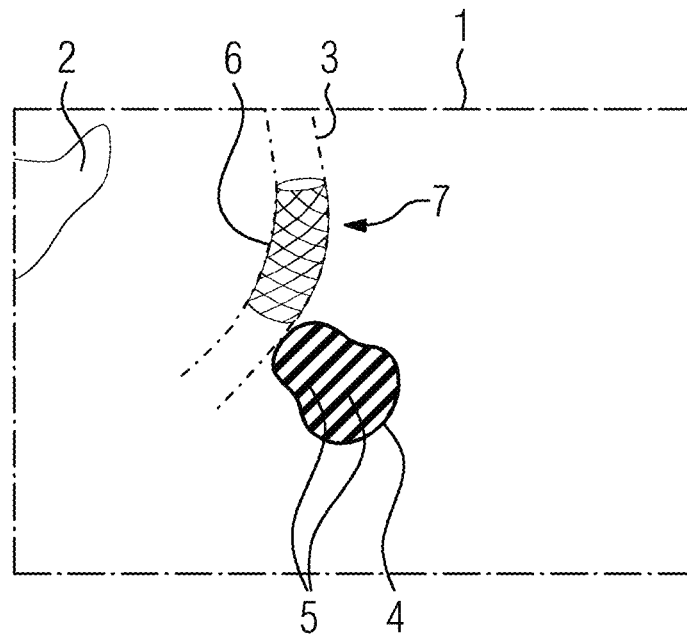
FIG. 2 depicts an example of a schematic diagram of a medical image dataset.

FIG. 2 depicts a schematic diagram of such a medical image dataset 1. Anatomical structures, for instance a bone 2 and the approximate course 3 of the blood vessel, are shown weakly discernible, e.g., with low intensity or low image values in the respective image points. Metallic coils 5 introduced into an aneurysm 4 are very clearly discernible. On the other hand, the stent 6 as the medical device 7 to be enhanced, which although visible may not be completely, or sufficiently accurately, discernible in terms of its contrast, appears significantly fainter.

In act S2, a user therefore selects via an input device of the medical imaging apparatus that stents 6 are meant to be displayed enhanced in the medical image dataset 1. The stent 6, or other objects to be enhanced, which may moreover also be anatomical structures such as bones, is assigned in this act certain selection or filter parameters, which define more precisely the image processing process that now follows, and parameterize said process so as to result in an enhanced display of the stent 6 in a result dataset.

To this end, in act S3, a non-linear low-pass filter, (e.g., a bilateral filter or a weighted median filter), is applied to image points of the image dataset 1 which belong to an image-value interval that describes the display of a stent 6 and hence was assigned to the stent 6 as a selection and filter parameter. A selection criterion may be used for this purpose, for example, which selects the image point for filtering if its image value lies in the image-value interval. In addition, a further selection criterion may also detect and likewise select individual outriders, e.g., image points located inside an area of image values that lie in the image-value interval, which image points have image values that lie alone outside the image-value interval. The selected image points are then filtered by the non-linear low-pass filter.

The non-linearity of the low-pass filter, and also in the two examples given of a low-pass filter, manifests itself here specifically in image values of adjacent image points which lie within a filter mask of the low-pass filter, which image values diverge widely from the image value of an image point to be filtered, being weighted less in the filtering. In principle, such image values and hence their image points may be ignored in the filtering or else still included but with lower weighting. The standard deviation defined by the noise may be used here as a measure of permitted divergences. It is thereby possible to avoid in particular any influence of adjacent, widely divergent structures, for example, of metal structures such as the coils 5, on the filtering, so that artifacts or error enhancements may also be reduced in this regard. In addition, this at least reduces any noise amplification.

The result of the low-pass filtering on the selected image points is an interim dataset, which in the present case also still includes the unfiltered portions of the image dataset 1. In act S4, the interim dataset is used to determine an enhancement dataset by subtracting the interim dataset from the image dataset 1. Because entire areas that do not contain the stent 6 of the object to be enhanced are not filtered, these areas drop out entirely, with the result that only the stent 6 to be enhanced is retained in the enhancement dataset, in the most accurate possible pose and extent of said stent.

In act S5, the result dataset is generated by adding the enhancement dataset to the image dataset 1, weighted by a weighting value, (e.g., a coefficient), that is greater than zero. The result dataset determined in this way may be output in act S6.

Figure 3:
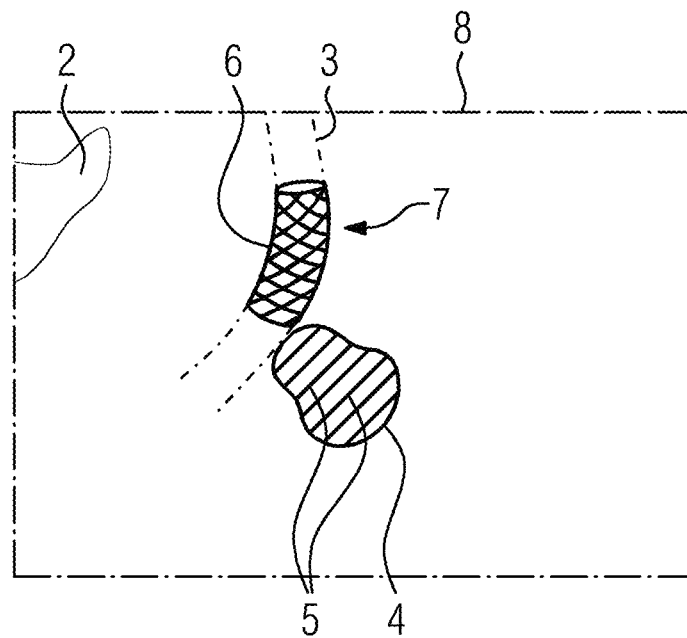
FIG. 3 depicts an example of a schematic diagram of a result dataset.

FIG. 3 depicts a schematic diagram of said result dataset 8. This shows that the clearly bounded and contrasted stent 6 as the medical instrument 7 to be enhanced is significantly more discernible than the anatomical structures and in particular also than the coils 5 in the aneurysm 4.

Amongst other options, in particular in addition to being stored, the output of the result dataset may be displayed by a display device of the medical imaging apparatus, e.g., by a visual monitor. An output as a VRT, MIP, thin-slab MIP, MPR, and the like is conceivable here.

Figure 4:
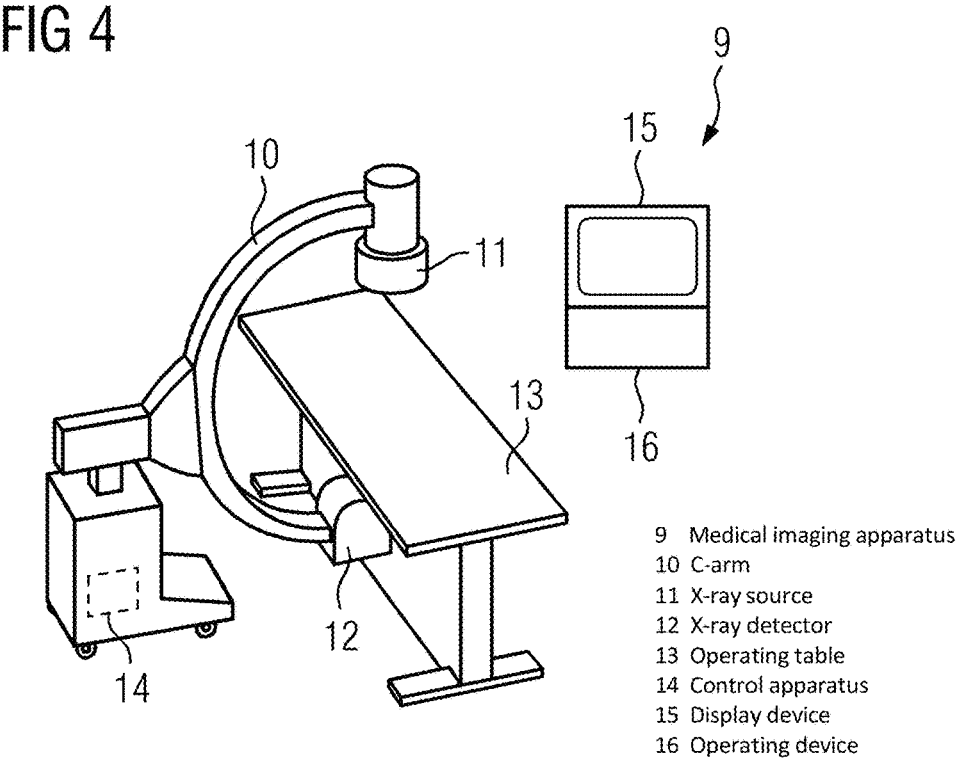
FIG. 4 depicts an example of a medical imaging apparatus.

FIG. 4 depicts an exemplary embodiment of a medical imaging apparatus 9, which in the present case is in the form of an X-ray apparatus having a C-arm 10, on which an X-ray source 11 and an X-ray detector 12 are arranged opposite one another. The medical imaging apparatus 9 is suitable for use in surgical interventions and therefore assigned to an operating table 13.

The operation of the X-ray apparatus 9 is controlled by a control apparatus 14, which is also configured to perform the method. A display device 15, (e.g., a visual monitor), may be used for displaying the result dataset. User inputs may be made via an operating device 16.

Figure 5:
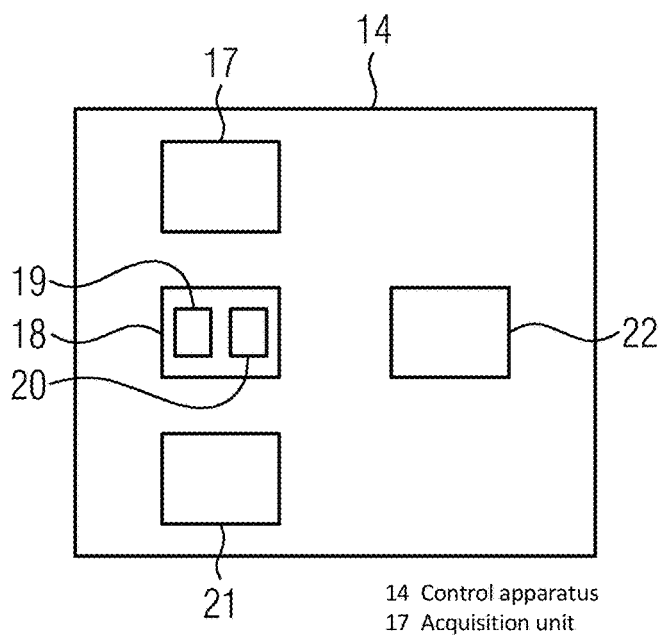
FIG. 5 depicts an example of the functional structure of a control apparatus of the medical imaging apparatus.

FIG. 5 depicts the functional structure of the control apparatus 14 in greater detail. In addition to an acquisition unit 17 that controls the acquisition operation of the imaging apparatus 9 in a generally known manner, the control apparatus includes a filter unit 18 for performing acts S3 and S4, which in turn includes a low-pass filtering sub-unit 19 for performing act S3 and a subtraction sub-unit 20 for performing act S4. The enhancement dataset determined in the filter unit 18 is used in a determination unit 21 for performing act S5, (e.g., to determine the result dataset), which may be displayed via an output unit 22, for instance on the display device 15 (act S6).

The filter unit 18 and the determination unit 21 are in particular image processors, whereas the output unit 22 may be, or may include, an output interface.

Although the disclosure has been illustrated and described in detail using the exemplary embodiments, the disclosure is not limited by the disclosed examples, and a person skilled in the art may derive other variations therefrom without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for image-processing an image dataset acquired from a patient by a medical imaging apparatus, wherein the image dataset comprises image values associated with image points, and depicts an acquisition region of the patient containing at least one object to be enhanced, which is represented by image values within an image-value interval, wherein the method comprises:
determining a non-linearly high-pass filtered enhancement dataset from a subsection of the image dataset confined to an image portion of the image dataset containing image values lying in the image-value interval, wherein the image portion of the image dataset contains the at least one object to be enhanced;
generating a result dataset by direct enhancement of the image dataset with the non-linearly high-pass filtered enhancement dataset, wherein the non-linearly high-pass filtered enhancement dataset is added to the image dataset, and wherein the non-linearly high-pass filtered enhancement dataset is weighted by a weighting value comprising a value that is greater than zero, the weighting value defining a magnitude of the non-linearly high-pass filtered enhancement dataset; and
outputting the result dataset.

2. The method of claim 1, wherein the medical imaging apparatus is an X-ray apparatus.

3. The method of claim 1, wherein the at least one object comprises a medical device.

4. The method of claim 3, wherein the medical device is a stent.

5. The method of claim 1, wherein the determining of the non-linearly high-pass filtered enhancement dataset comprises:
determining an interim dataset by applying a non-linear low-pass filter to image points satisfying a selection condition that evaluates image values, wherein the selection condition selects an image point when an image value of the image point lies within the image-value interval; and
determining the non-linearly high-pass filtered enhancement dataset by subtracting the interim dataset from the image dataset pixel by pixel.

6. The method of claim 5, wherein, for the applying of the non-linear low-pass filter, image points lying within a filter mask being used around an image point under consideration are rated according to a difference between an image value of the image points lying within the filter mask and the image value of the image point under consideration,
wherein more widely divergent image values result in a lower weighting, and
wherein the applying of the non-linear low-pass filter is performed based on the rating, a bilateral filter is used as the non-linear low-pass filter, a weighted median filter is used as the non-linear low-pass filter, or a combination thereof.

7. The method of claim 6, wherein the image-value interval is selected such that anatomical structures, medical aids, or a combination thereof in the acquisition region that do not correspond to the object are not selected for filtering.

8. The method of claim 7, wherein the medical aids comprise coils in an aneurysm.

9. The method of claim 6, wherein the weighting value is a coefficient in a range of 1 to 20.

10. The method of claim 1, wherein the image-value interval is selected such that anatomical structures, medical aids, or a combination thereof in the acquisition region that do not correspond to the object are not selected for filtering.

11. The method of claim 10, wherein the medical aids comprise coils in an aneurysm.

12. The method of claim 1, wherein the weighting value is a coefficient in a range of 1 to 20.

13. The method of claim 1, wherein the image dataset is three-dimensional and exists in a form of sectional images or slice images,
   wherein an associated result image of the result dataset is determined successively for all the sectional images or the slice images.

14. The method of claim 13, wherein the result dataset is displayed in a volume-rendered manner, as a thin-slab maximum intensity projection, as a multiplane reconstruction, or a combination thereof.

15. The method of claim 1, wherein the result dataset is displayed in a volume-rendered manner, as a thin-slab maximum intensity projection, as a multiplane reconstruction, or a combination thereof.

16. A non-transitory electronically readable data storage medium on which a computer program is stored, wherein the computer program, when executed by a medical imaging apparatus, causes the medical imaging apparatus to:
   acquire an image dataset from a patient, the image dataset comprising image values associated with image points and depicting an acquisition region of the patient containing at least one object to be enhanced, which is represented by image values within an image-value interval;
   determine a non-linearly high-pass filtered enhancement dataset from a subsection of the image dataset confined to an image portion of the image dataset containing image values lying in the image-value interval, wherein the image portion of the image dataset contains the at least one object to be enhanced;
   generate a result dataset by direct enhancement of the image dataset with the non-linearly high-pass filtered enhancement dataset, wherein the non-linearly high-pass filtered enhancement dataset is added to the image dataset, and wherein the non-linearly high-pass filtered enhancement dataset is weighted by a weighting value comprising a value that is greater than zero, the weighting value defining a magnitude of the non-linearly high-pass filtered enhancement dataset; and
   output the result dataset.

17. The method of claim 1, wherein image points around an image point under consideration within the image portion are rated according to a difference between the respective image values of the image points and an image value of the image point under consideration, and wherein a non-linear filtering is performed based on the ratings in the determining of the non-linearly high-pass filtered enhancement dataset.

18. A medical imaging apparatus comprising:
   a control apparatus configured to:
   acquire an image dataset from a patient, the image dataset comprising image values associated with image points and depicting an acquisition region of the patient containing at least one object to be enhanced, which is represented by image values within an image-value interval;
   determine a non-linearly high-pass filtered enhancement dataset from a subsection of the image dataset confined to an image portion of the image dataset containing image values lying in the image-value interval, wherein the image portion of the image dataset contains the at least one object to be enhanced;
   generate a result dataset by direct enhancement of the image dataset with the non-linearly high-pass filtered enhancement dataset, wherein the non-linearly high-pass filtered enhancement dataset is added to the image dataset, and wherein the non-linearly high-pass filtered enhancement dataset is weighted by a weighting value comprising a value that is greater than zero, the weighting value defining a magnitude of the non-linearly high-pass filtered enhancement dataset; and
   output the result dataset.

\* \* \* \* \*